US006043057A

United States Patent [19]

[11] Patent Number: 6,043,057
[45] Date of Patent: Mar. 28, 2000

Holmgren et al.

[54] RECOMBINANT SYSTEMS FOR EXPRESSION OF THE CHOLERA B-SUBUNIT WITH THE AID OF FOREIGN PROMOTERS AND/OR LEADER PEPTIDES

[75] Inventors: Jan Holmgren, Västra Frölunda, Sweden; Joaquin Sanches Castillo, Cuernavaca, Mexico

[73] Assignee: Vitec Aktiebolag, Vastra Frolunda, Sweden

[21] Appl. No.: 08/844,849

[22] Filed: Apr. 22, 1997

Related U.S. Application Data

[63] Continuation of application No. 08/371,896, Jan. 12, 1995, abandoned, which is a continuation of application No. 08/098,132, Jul. 26, 1993, abandoned, which is a continuation of application No. 07/912,075, Jul. 8, 1992, Pat. No. 5,268,276, which is a continuation of application No. 07/408,758, Sep. 18, 1989, abandoned.

[30] Foreign Application Priority Data

Sep. 16, 1988 [SE] Sweden .................................. 8803291

[51] Int. Cl.[7] ............................ C07K 19/00; C12N 15/62

[52] U.S. Cl. .................. 435/69.7; 435/252.3; 435/320.1; 530/350; 536/23.4

[58] Field of Search ................................ 435/69.7, 252.7, 435/320.1; 530/350; 536/23.4

[56] References Cited

U.S. PATENT DOCUMENTS

| | | | |
|---|---|---|---|
| 4,411,888 | 10/1983 | Klipstein et al. | 424/92 |
| 4,431,739 | 2/1984 | Riggs | 435/253.1 |
| 4,634,678 | 1/1987 | Salstrom et al. | 435/317 |
| 4,652,639 | 3/1987 | Stabinsky | 536/23.1 |
| 4,666,837 | 5/1987 | Harford et al. | 435/68 |
| 4,751,064 | 6/1988 | Sela | 424/92 |
| 4,808,700 | 2/1989 | Anderson et al. | 530/403 |
| 4,882,278 | 11/1989 | Mekalanos | 435/172.3 |
| 5,066,596 | 11/1991 | Manning et al. | 435/252.33 |
| 5,182,109 | 1/1993 | Tamura et al. | 424/92 |
| 5,223,610 | 6/1993 | Burton | 536/24 |

FOREIGN PATENT DOCUMENTS

| | | |
|---|---|---|
| 0095452 | 11/1983 | European Pat. Off. . |
| 0119031 | 2/1984 | European Pat. Off. . |
| 0125228 | 4/1984 | European Pat. Off. . |
| 0168322 | 1/1986 | European Pat. Off. . |
| 0251579 | 6/1987 | European Pat. Off. . |
| 0429816 | 6/1991 | European Pat. Off. . |
| WO 8606635 | 11/1986 | WIPO . |
| WO 9003437 | 4/1990 | WIPO . |
| WO 9101146 | 2/1991 | WIPO . |
| WO 9107979 | 6/1991 | WIPO . |
| WO 9109871 | 7/1991 | WIPO . |
| WO 9200099 | 1/1992 | WIPO . |
| WO 9219265 | 11/1992 | WIPO . |

OTHER PUBLICATIONS

Aoki et al, *Infect. and Immun.* 53(3):587–594, Sep. 1986.

Amana et al, *Gene* 25:167–178, 1983.

Guzman–Verduzco et al., *J. Bact.* 169(11):5201–5208, Nov. 1987.

J. of Immunol. 141:1495–1501 (Sep. 1, 1988) Liang et al. Oral Administration of Chlolera Toxins and as Virus Conjugation Potentiates Gut and Respiratory Immunity Against send es Virus.

Cholera Toxin B–Subunit Gene Fusion: Structural and Functional Analysis of the Chimeric Protein, Dertzbaugh, et al., *Infection and Immunology*, 58: No. 1. 70–79, Jan. 1990.

From Cholera Toxin to Subunit Vaccines, Holmgren, *Current Science*, 59: Nos 13 & 14, 665–669. Jul. 1990.

Fusion Proteins Containing the A2 Domain of Cholera Toxin Assemble with B Polypeptides of Cholera Toxin to Form Immunoreactive and Functional Holotoxin–Like Chimeras, Jobling, et al., *Infection and Immunity, 60*: No. 11, 4915–4924, Nov. 1992.

Current progress in the development of the B subunits of cholera toxin and *Escherichia coli* heat–labile enterotoxin as carriers for the oral delivery of heterologous antigens and epitopes, Nashar, et al., *Vaccine*, 11: Issue 2, 235–240, 1993.

Immunological characterization of a rotavirus–neutralizing epitope fused to the cholera toxin B subunit, González, et al., *Gene*, 133: 227–232, 1993.

Comparative Effectiveness of the Cholera Toxin B Subunit and Alkaline Phosphatase as Carriers for Oral Vaccines, Dertzbaugh, et al., *Infection and Immunity*, 61: No. 1, 48–55, Jan. 1993.

Strategies for the Induction of Immune Responses at Mucosal Surfaces Making Use of Cholera Toxin B Subunit as Immunogen, Carrier, and Adjuvant, Holmgren, et al., *American Journal of Tropical Medicine and Hygiene*, Suppl. 1994, 42–54.

Structure and arrangement of the cholera toxin genes in *Vibro cholerae* 0139, Lebens, et al., *EEMS Microbiology Letters*, 117: 197–202, 1994.

Construction of Mucosal Immunogen by Gene Fusion of Protein Antigen and Cholera Toxin Segments, Hajishengallis, et al., "Abstracts of the Annual Meeting of the American Society for Microbiology", E–31, May 23–27, 1994.

DeBoer, H.A. et al., *Proc. Natl. Acad. Sci. USA 80*:21–25, 1983.

Lockman, H. et al., *J. of Biol. Chem. 258*(22):13722–13726, 1983.

McKenzie, S.J. et al., *J. of Immunol. 133*(4):1818–1824, 1984.

(List continued on next page.)

*Primary Examiner*—John Ulm
*Attorney, Agent, or Firm*—Knobbe, Martens, Olson & Bear, LLP

[57] ABSTRACT

Disclosed herein are procedures whereby with the aid of recombinant DNA methods, the expression of the binding subunit protein of cholera toxin (CTB) or derivatives thereof including hybrid gene fusion proteins to CTB has been brought under the control of a foreign (non-cholera toxin) promoter and/or the CTB protein or its derivatives being synthesized with a foreign rather than the natural leader peptide to facilitate translocation across cell membranes.

29 Claims, 9 Drawing Sheets

OTHER PUBLICATIONS

Mekalanos, J.J. et al., *Nature 306*:551–557, 1983.

Nishi, T. et al., *DNA 2*(4):265–273, 1983.

Okamoto, K. et al., *Infect. & Immun. 56*(8):2144–2148, 1988.

Sanchez, J. et al., *FEBS 4206 208*(2):194–198, 1986.

Studier, F. William, *J. Mol. Biol. 189*:113–130, 1986.

Tabor, S. et al., *Proc. Natl. Acad. Sci. USA 82*:1074–1078, 1985.

Tacon, W.C.A. et al., *Gene 23*:255–265, 1983.

Old, "Principles of Gene Manipulation, Studies in Microbiology,"vol. 2 (Blackwell Scientific Pub., London)(1979).

Miller et al., "Synthesis of Cholera Toxin is Positively regulated at the Transcriptional Level by ToxR," PNAS (USA) 81:3471–3475 (Jun. 1984).

Sanchez et al., "Recombinant System for Overexpression of Cholera Toxin B Subunit in *Vibrio Cholerae* as a Basis for Vaccine Development," PNAS (USA) 86:481–485 (1989).

Sanchez, et al., "Recombinant Fusion Protein for Simple Detection of *Escherichia Coli* Heat–Stable Enterotoxin by GM1 Enzyme–Linked Immunosorbent Assay," J. Clinical Microbiology, 28(10) :2175–2177 (Oct. 1990).

Czerkinsky, et al., "Oral Administration of a Streptococcal Antigen Coupled to Cholera Toxin B Subunit Evokes Strong Antibody Responses in Salivary Glands and Extramucosal Tissues," Infection and Immunity, 57(4) :1072–1077 (Apr. 1989).

Czerkinsky, et al., "Antibody–Producing Cells in Peripheral Blood and Salivary Glands after Oral Cholera Vaccination of Humans," Infection and Immunity, 59(3) :996–1001 (Mar. 1991).

Holmgren, et al., "Cholera as a Model for Research on Mucosal Immunity and Development of Oral Vaccines," Current Opinion in Immunology, 4:387–491 (1992).

Holmgren, et al., "An Oral B Subunit: Whole Cell Vaccine Against Cholera," Vaccine, 10(13) :911–914 (1992).

Holmgren, et al., "Cholera Toxin and Cholera B Subunit as Oral—Mucosal Adjuvant and Antigen Vector Systems," Vaccine, 11(12) :1179–1184 (1993).

Quiding, et al., "Intestinal Immune Responses in Humans," J. Clin. Invest. 88:143–148 (Jul. 1991).

Holmgren, et al., "Mucosal Immunity: Implications for Vaccine Development," Immunobiol., 184:157–179 (1992).

Lebens, et al., "Large–Scale Production of *Vibrio Cholerae* Toxin B Subunit for Use in Oral Vaccines," Bio/Technology, 11:1574–1578 (Dec. 1993).

Shin–ichi Tamura et al., "Protection against influenza virus infection by vaccine inoculated intranasally with cholera toxin B subunit", Vaccine, 6:409–413, Oct. 1988.

J. Sanchez et al., "Genetic fusion of a non–toxic heat–stable enterotoxin–related decapeptide antigen to cholera toxin B–subunit", FEBS Letters, 241(1,2) :110–114, Dec. 1988.

Construction of Novel Cloning Vectors for Creating Translational Fusions with the B Subunit of Cholera Toxin, Dertzbaugh, et al., "Abstracts, 1987 Extrachromosomal Genetic Elements Meeting", p. 256, 1987.

Overexpression of the B–subunit of cholera toxin by the tac promoter in *Escherichia coli* and *Vibrio cholerae*., Sanchez, et al., "Abstracts of the Annual Meeting of the American Society for Microbiology—1988", D–175.

Coordinated assembly of multisubunit proteins: Oligomerization of bacterial enterotoxins in vivo and in vitro, Hardy, et al., *Proc. Natl. Acad. Sci. USA*, 85: 7109–7113, Oct. 1988.

Plasmid vectors for constructing translational fusions to the B subunit of cholera toxin, Dertzbaugh, et al., *Gene*, 82: 335–342, 1989.

Fusion of Genes Encoding *Escherichia coli* Heat–Stable Enterotoxin and Outer Membrane Protein OmpC, Saarilahti, et al., *Infection and Immunity*, 57: 3663–3665, Nov. 1989.

Internasal Immunization of Mice with Recombinant Protein Antigen of Serotype c Streptococcus Mutans and Cholera Toxin B Subunit, Takahashi, et al., *Archs oral Biol.*, 35: No. 6, 475–477, 1990.

| -3 | -2 | -1 | +1 | ★ | ★ |
|---|---|---|---|---|---|
| Ala | His | Gly | Ala | Pro | Gly |
| GCA | CAC | GGA | GCT | CCC | GGG |

| -4 | -3 | -2 | -1 | +1 | +2 |
|---|---|---|---|---|---|
| Tyr | Ala | His | Gly | Thr | Pro |
| TAT | GCA | CAT | GGA | ACA | CCT |

```
                                                               -20
       SD          Met Asn Lys Val Lys Phe Tyr Val Leu Phe Thr Ala Leu
AATTCGGGATGAATT    ATG AAT AAA GTA AAA TTT TAT GTT TTA TTT ACG GCG TTA

                       -10         (+1)  *   * ↓   ↓           -1  +1
Leu Ser Ser Leu Cys Ala His Gly Ala Pro Gly Tyr Ala His Gly Thr Pro
CTA TCC TCT CTA TGT GCA CAC GGA GCT CCC GGG TAT GCA CAT GGA ACA CCT

                              10                                (Tyr)
Gln Asn Ile Thr Asp Leu Cys Ala Glu Tyr His Asn Thr Gln Ile His Thr
CAA AAT ATT ACT GAT TTG TGT GCA GAA TAC CAC AAC ACA CAA ATA CAT ACG

20    (Asn)                                 30
Leu Asn Asp Lys Ile Phe Ser Tyr Thr Glu Ser Leu Ala Gly Lys Arg Glu
CTA AAT GAT AAG ATA TTT TCG TAT ACA GAA TCT CTA GCT GGA AAA AGA GAG
```

FIG. 2A

```
            40                                        (Ile)      50
Met Ala Ile Ile Thr Phe Lys Asn Gly Ala Thr Phe Gln Val Glu Val Pro
ATG GCT ATC ATT ACT TTT AAG AAT GGT GCA ACT TTT CAA GTA GAA GTA CCA

(Ser) 60                                                          (Asn)
 Gly Ser Gln His Ile Asp Ser Gln Lys Lys Ala Ile Glu Arg Met Lys Asp
 GGT AGT CAA CAT ATA GAT TCA CAA AAA AAA GCG ATT GAA AGG ATG AAG GAT

                                     80
Thr Leu Arg Ile Ala Tyr Leu Thr Glu Ala Lys Val Glu Lys Leu Cys Val
ACC CTG AGG ATT GCA TAT CTT ACT GAA GCT AAA GTC GAA AAG TTA TGT GTA

        90                                           100
Trp Asn Asn Lys Thr Pro His Ala Ile Ala Ala Ile Ser Met Ala Asn End
TGG AAT AAT AAA ACG CCT CAT GCG ATT GCC GCA ATT AGT ATG GCA AAT TAA

GATATAAAAAGCCCACCTCAGTGGGCTTTTTT
```

FIG. 2B

```
      +   +   +   *   *   *   *   *   *
     Arg Ile His Cys Ala Glu Leu Cys Cys
agct **AGA ATT CAC TGC GCT GAA TTG TGT TGT**

 *   *   *   *   +   +   +   +   +   +
Asn Pro Ala Cys Pro Gly Tyr Ala His Gly
AAT CCT GCA TGC Ccc ggg tat gca cat gga

+1
Thr
```

FIG. 6

RECOMBINANT SYSTEMS FOR EXPRESSION OF THE CHOLERA B-SUBUNIT WITH THE AID OF FOREIGN PROMOTERS AND/OR LEADER PEPTIDES

This application is a continuation of U.S. patent application Ser. No. 08/371,896, filed Jan. 12, 1995, now abandoned, which was a continuation of U.S. patent application Ser. No. 08/098,132, filed Jul. 26, 1993, now abandoned, which was a continuation of U.S. patent application Ser. No. 07/912,075, filed Jul. 8, 1992, now issued U.S. Pat. No. 5,268,576, which was a continuation of U.S. patent application Ser. No. 07/408,758, filed Sep. 18, 1989 now abandoned.

BACKGROUND OF THE INVENTION

*Vibrio cholerae* of serogroup O1 may induce severe diarrhoeal disease when multiplying in the gut of infected individuals by releasing cholera toxin (CT) which induces active electrolyte and water secretion from the intestinal epithelium. By analogous mechanisms several other bacteria, for instance *Escherichia coli*, may also cause diarrhoea by releasing other enterotoxins that may be related or unrelated to CT. CT is the prototype bacterial enterotoxin. It is a protein built from two types of subunits: a single A subunit of molecular weight 28,000 and five B subunits, each with a molecular weight of 11,600. The B subunits are aggregated in a ring by tight noncovalent bonds; the A subunit is linked to and probably partially inserted in the B pentamer ring through weaker noncovalent interactions. The two types of subunits have different roles in the intoxication process: the B subunits are responsible for cell binding and the A subunit for the direct toxic activity. The molecular aspects of toxin binding to intestinal and other mammalian cells and of the subsequent events leading to activation of adenylate cyclase through the intracellular action of the A subunit (and its A1 fragment) have been clarified in considerable detail (see J Holmgren, Nature 292:413–417, 1981). More recently information has also become available on the genetics and biochemistry of cholera toxin synthesis, assembly and secretion by *V. cholerae* bacteria. CT is encoded by chromosomal structural genes for the A and B subunits, respectively. These genes have been cloned from several strains, and their nucleotide sequences have been determined. The genes for the A and B subunits of CT are arranged in a single transcriptional unit with the A cistron (ctxA) preceeding the B cistron (ctxB) . Studies on the organization of CT genes in *V. cholerae* strains of classical and El Tor biotypes have suggested that there are two copies of CT genes in classical biotype strains while there is only one copy in most El Tor strains (J J Mekalanos et al, Nature 306:551–557, 1983). The synthesis of CT is positively regulated by a gene, toxR that increases ctx expression manifold (V L Miller and J J Mekalanos, Proc Natl Acad Sci USA, 81:3471–3475, 1984). ToxR acts at the transcriptional level, and is present in strains of both classical and El Tor biotypes. ToxR probably increases ctx transcription by encoding a regulatory protein that interacts positively with the ctx promoter region. Studies on heat-labile enterotoxin (LT) in *Escherichia coli* (the subunit structure and function of LT is closely similar but not identical to CT) have shown that the A and B subunits are initially synthesized as precursors with a leader peptide preceeding the mature subunit proteins. These precursors are rapidly processed (i.e. the leader peptide is being removed) and translocated across the inner membrane into the periplasm, where unassembled monomeric B subunits pentamerize and associate with A subunit with a half-time of 1–2 min. The pathway of toxin assembly appears to proceed via A subunit association with B monomers or small oligomers. Once the complete toxin has assembled, in *V. cholerae* (in contrast to *E. coli* where the toxin remains in the periplasm the toxin is being translocated (secreted) across the *V. cholerae* O1 outer membrane through some sort of interaction of B subunit domains with the outer membrane (T R Hirst & J Holmgren, Proc Natl Acad Sci USA, 84:7418–7422, 1987; S J S Hardy et al, ibid, in press, 1988). If the B subunits of CT or LT are being expressed in the absence of any A subunit (several such strains have been prepared by chemical mutagenesis or deletions by recombinant DNA methods in the ctxA or eltA cistrons) the B subunits form pentamers which are then secreted from *V. cholerae* via the same pathway as for the intact toxin except for an apparently slightly slower assembly process in the periplasm (T R Hirst et al, Proc Natl Acad Sci USA 81:2645–2649, 1984; S J S Hardy et al, ibid, in press, 1988). Because vaccination against cholera by parenteral injection has yielded only modest and short-term protection (usually less than 50% protection for less than 6 months), attention has turned to development of oral vaccines that stimulate intestinal immunity more efficiently. Special attention has been drawn to CTB pentamers as one component of such oral cholera vaccines (J Holmgren et al., Nature 269:602–604, 1977). CTB is an effective oral immunizing agent which in a large field trial has been shown to afford protection against both cholera and diarrhoea caused by LT enterotoxigenic *E. coli* (J Clemens et al., Lancet ii:124–127, 1986; J Infect Dis, in press, 1988). The separation of B subunit from A excludes any risk of reversion to toxicity, and CTB has been administered orally to more than 25,000 people without any side effects. These features have made CTB an important component, together with killed whole cholera vibrios, of a new oral cholera vaccine. Moreover, CTB has attracted much interest recently as an immunogenic carrier for various other peptide or carbohydrate antigens and has also been used as a receptor-blocking and receptor-modulating agent for short-term prophylaxis of cholera and *E. coli* diarrhoea (R I Glass et al, J Infect Dis 149:495–500, 1984; S T Donta et al, ibid 157:557–564, 1988; S J McKenzie and J F Halsey, J Immunol 133:1818–1824, 1984; A-M Svennerholm et al J Clin Microbiol 24:585–590, 1986).

These findings have emphasized a need to increase the yield of CTB for large-scale production, ideally avoiding at the same time the drawback in currently used preparation methods (see J L Tayot et al, Eur J Biochem 113:249–258, 1981) of having to purify the CTB protein from active toxin.

Therefore, with the aid of strategies and procedures described in this application we have constructed overexpression systems for CTB and CTB fusion proteins in which the CTB gene (or the gene for the hybrid fusion protein) is under control of strong foreign (non-cholera toxin) promoters. Our success in this regard contrasts with previous attempts by different procedures by J J Mekalanos et al (Nature 306:551–557, 1983) to attain this goal using one of the promoters (tacp) described in one of our examples, as these attempts were reported to fail since they resulted in expression of less CTB than achieved with the natural ctx promoter.

Figure 1A:
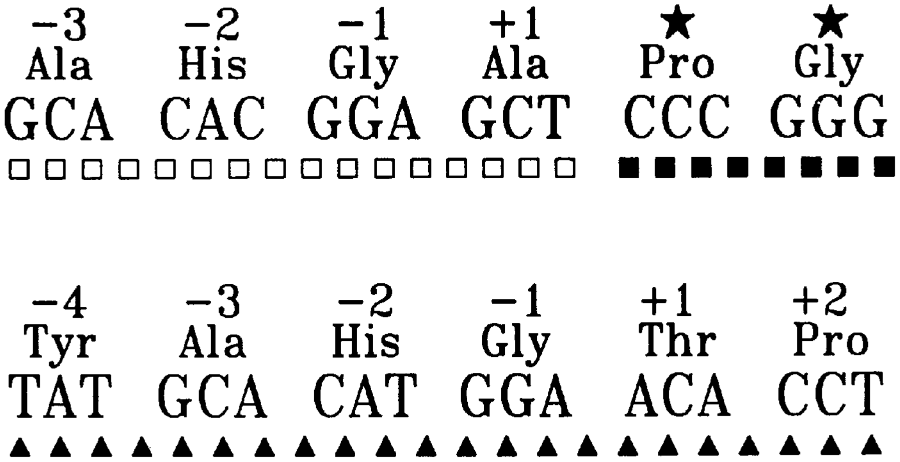
FIG. 1A is a diagrammatic representation of the fusion joint between the LTB and CTB genes.
Figure 1B:
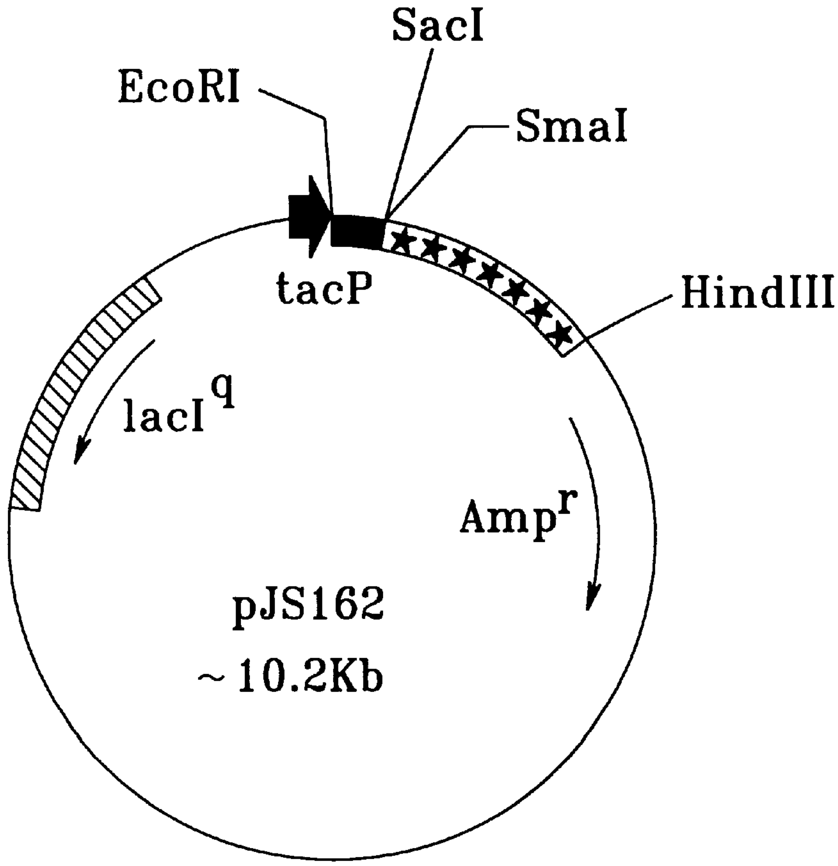

The FIG. 1B is a map of plasmid pJS162 with the CTB gene under the control of the tacp promoter.

FIGS. 2A and 2B is the diagram showing the nucleotide sequence of the CTB gene in plasmid pJS162.

Figure 3:
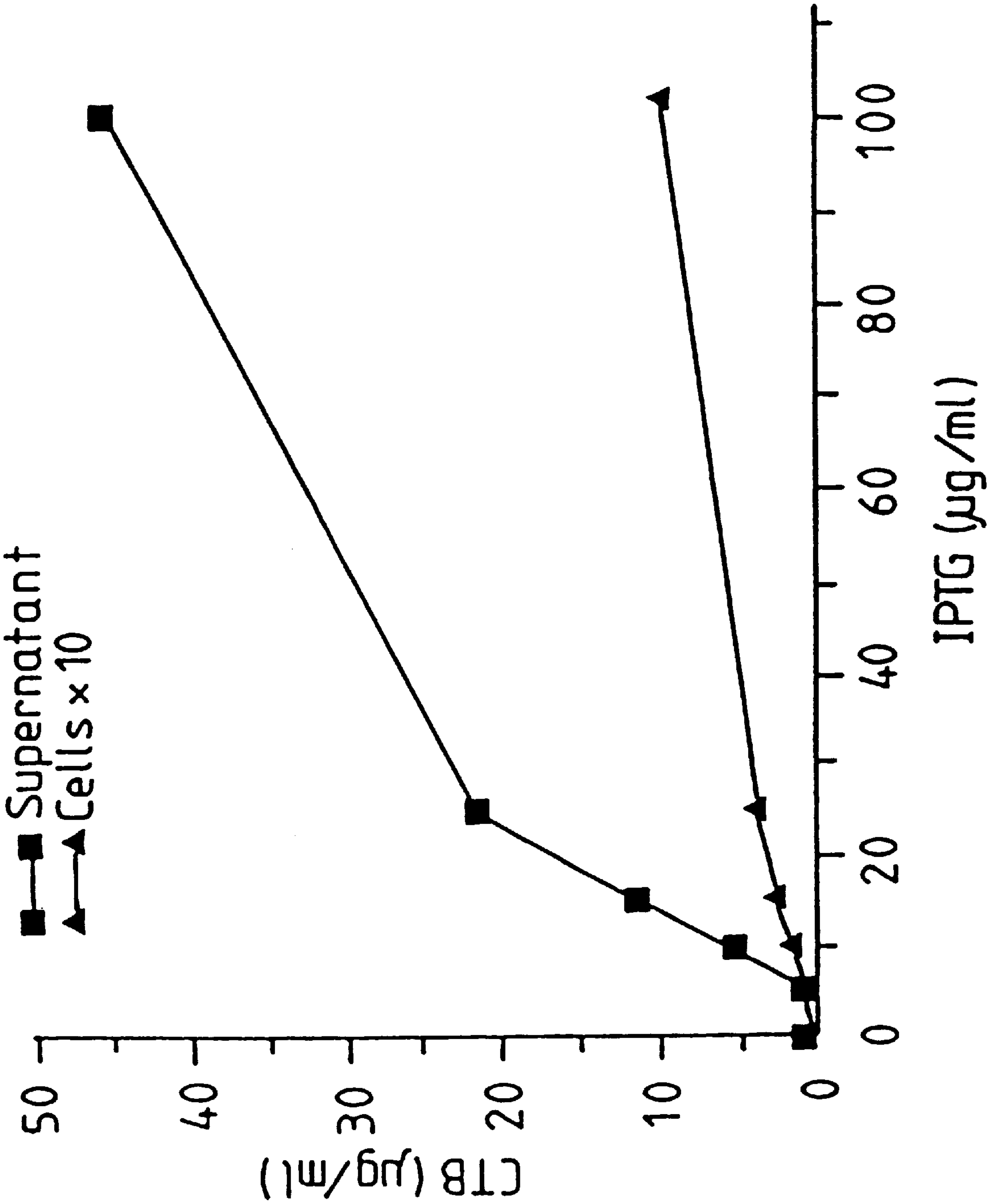

FIG. 3 is a graph showing the induction of CTB expression by IPTG in *V. cholerae* JBK70 (pJS162).

Figure 4:
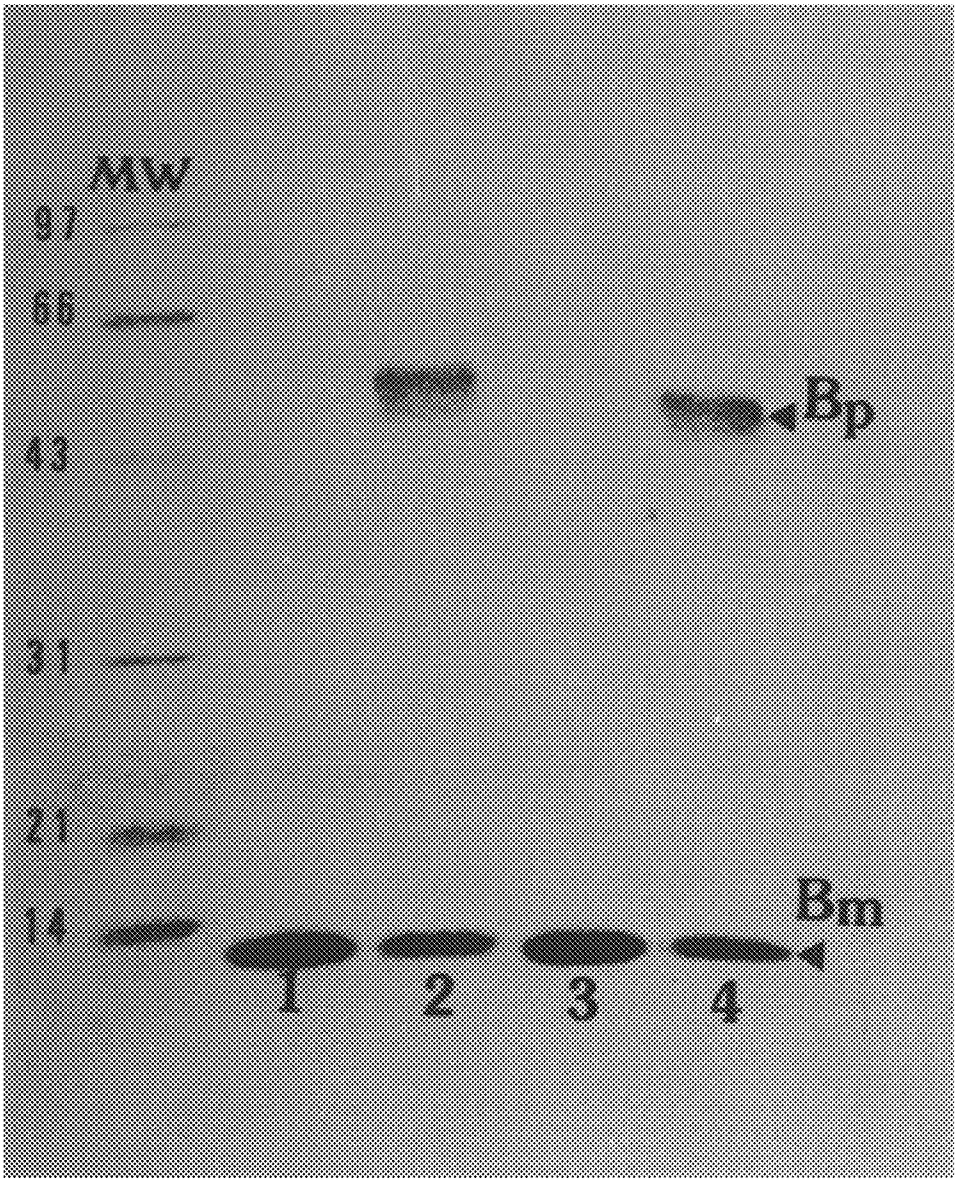

FIG. 4 is a polyacrylamide gel electrophoresis (PAGE) analysis of boiled and unboiled samples of CTB.

Figure 5:
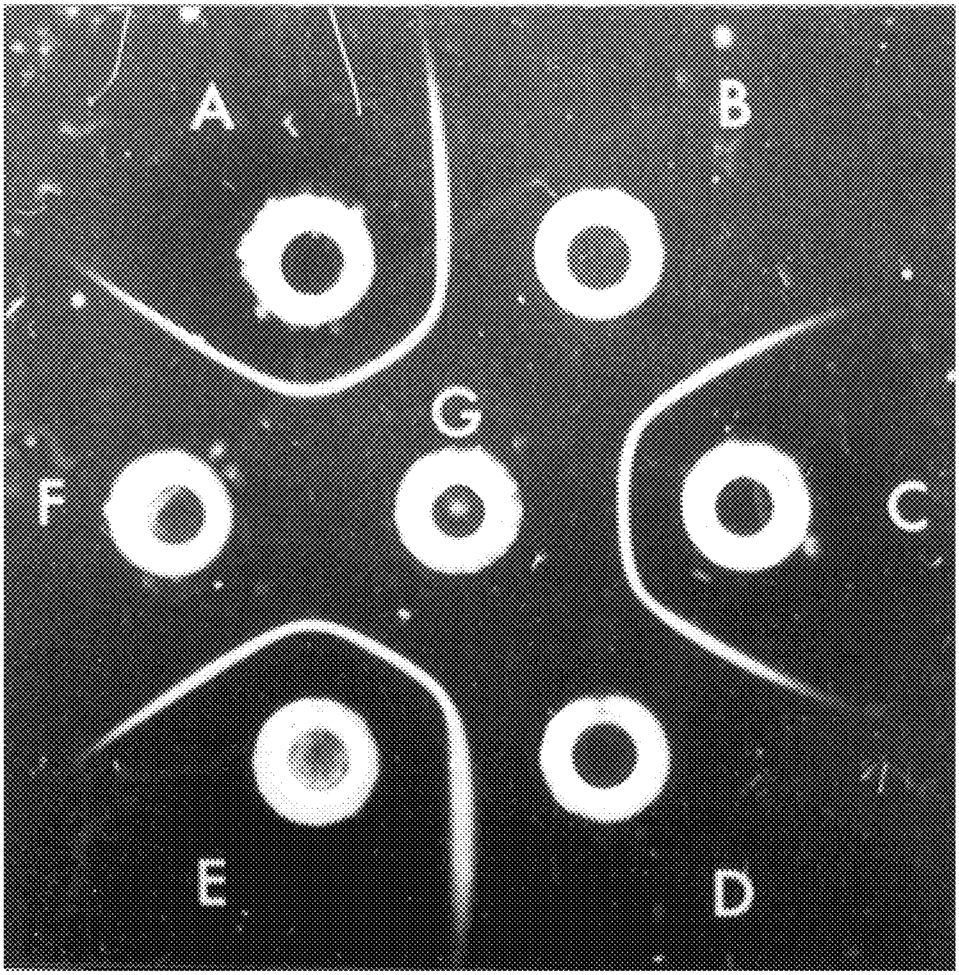

FIG. 5 is an Ouchterlong double-diffusion-in-gel analysis of 569B CTB and recombinant CTB reacted with rabbit antisera.

FIG. 6 is a diagrammatic representation of the fusion of an STa-related decapeptide to CTB.

Figure 7:
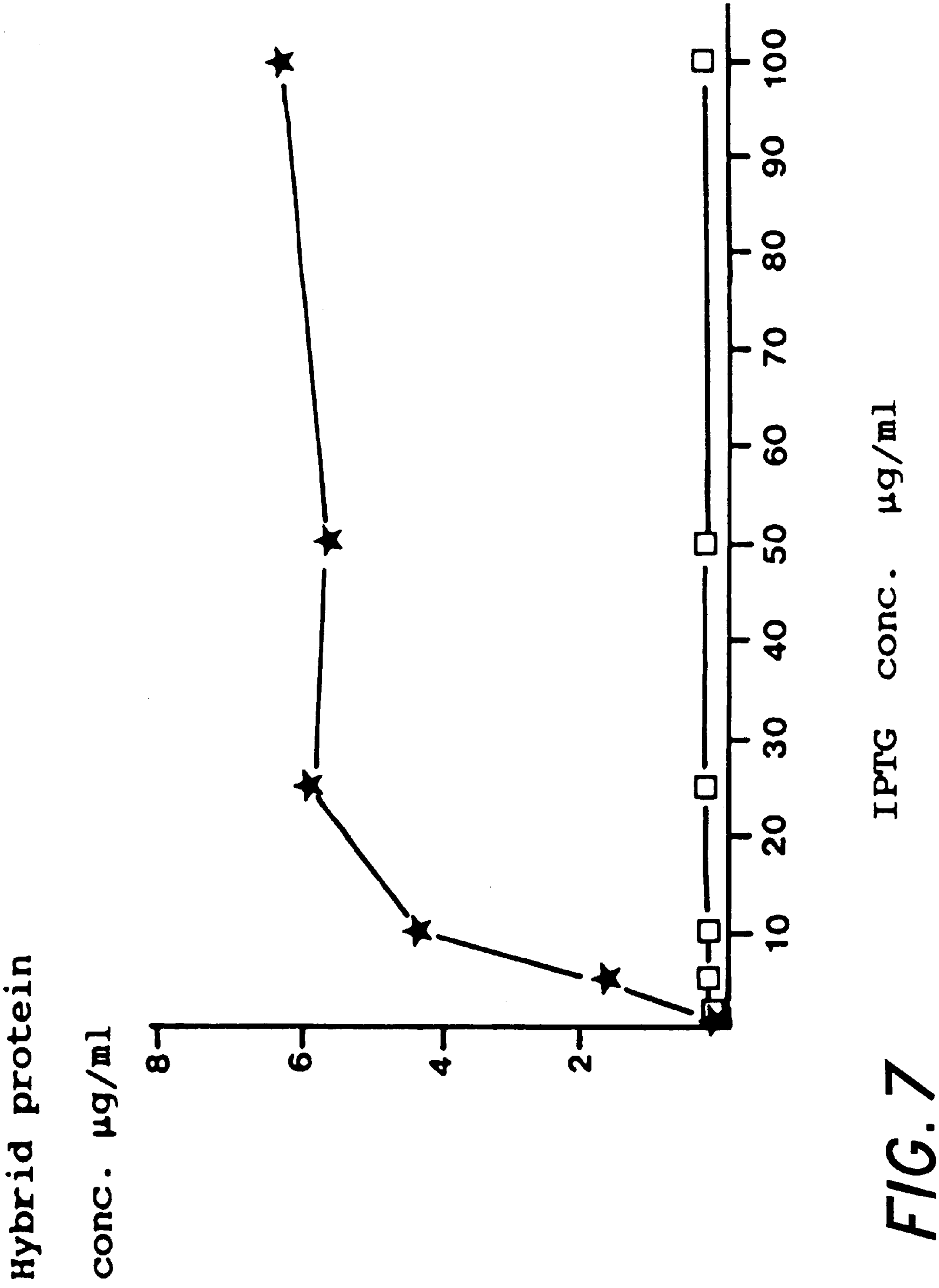

FIG. 7 is a graph showing the induction of STa-related decapeptide-CTB hybrid gene expression by IPTG in *V. cholerae* JBK70 harboring plasmid pJS8.

Figure 8:

FIG. 8 is an immuno-blotting analysis of the STa-related decapeptide CTB hydrid protein after SDS-PAGE followed by electrotransfer of separated proteins onto nitrocellulose paper.

SUMMARY OF THE INVENTION

By use of recombinant DNA methods we have achieved overexpression systems for the B subunit of cholera toxin (CTB) or CTB derivatives, including fusion proteins of CTB. Characteristically in these systems expression of the gene encoding CTB or CTB derivative proteins has been brought under the control of a strong foreign (non-cholera toxin) promoter in wide-host range plasmid vectors. The gene constructions described are independant of the natural CT promoter and toxR expression regulatory systems. Two such overexpression systems are exemplified, one in which CTB is expressed in an inducible or constitutive manner under the control of the tacP promoter, and another in which CTB expression is controlled by the T7 RNA polymerase dependent promoter. In those examples the gene constructions allowing overexpression are present in wide-host range plasmids. This allows production of high levels of CTB or CTB derivatives from different bacterial species, e.g. *E. coli* and *V. cholerae*, harbouring these plasmids. The acessibility of the foreign promoter overexpression systems for production of CTB derivatives in the form of fusion proteins is also being exemplified through the fusion of a synthetic DNA sequence encoding a non-toxic decapeptide, derived from the *E. coli* heat-stable enterotoxin (STa), to the CTB gene and expression of the gene fusion protein in *V. cholerae* under the control of the tacP promoter.

DETAILED DESCRIPTION OF THE INVENTION

Definitions and Abbreviations

The terms CTB and CTB derivatives as used in this application define any protein or peptide (with the exception of *E. coli* LTB) with properties that allow it to be recognized by immune serum (antiserum) prepared against the CTB protein encoded by the plasmid pJS162 described in this application.

The term foreign promoter defines any promoter characterized by being different from the natural ctx promoter.

The term foreign leader peptide defines any peptide sequence on a protein molecule which facilitates the translocation of a protein, in this application the translocation of CTB or CTB derivatives, across cell membranes characterized in that it is being different from the natural leader peptides for cholera toxin subunits.

The standard nomenclature as used in e. E-L Winnacker, From Genes to Clones, VCH Publishers, New York (1987) is adhered to for defining DNA restriction endonucleases, restriction sites and restriction sequences. Oligodeoxynucleotides and amino acids are referred to with the conventional one-letter and three-letter abbreviation codes.

EXAMPLES

Example 1

RECOMBINANT SYSTEM FOR INDUCIBLE OVEREXPRESSION OF CTB UNDER TACP CONTROL 1.1 Gene (DNA) manipulations for bringing the CTB gene under control of inducible tacP Based on theoretic al considerations and preliminary experimentation we assumed that overexpression of CTB from a foreign (non-cholera toxin) promoter might be achieved if the CTB gene could be brought as near the foreign promoters as possible, ideally avoiding any non-CTB encoding DNA of *V.cholerae* origin between the promoter and the CTB gene. In this example we describe procedures by which this strategy was used to construct a successful overexpression system for CTB production by placing the CTB gene under expression control of inducible tacp promoter.

The DNA encoding the *E.coli* LTB leader has a single EcoRI restriction site at its 5' end located just upstream the ribosome binding site which has been used recently to insert the LTB gene after the strong tacP promoter thus creating the plasmid PMMB68 (M Sandkvist et al, J Bacteriol 169: 4570–4576, 1987). To profit from this strategically located EcoRI site (which is missing in the CTB gene) for bringing the expression of CTB under control of the same promoter we decided to fuse genetically the mature CTB protein to the leader peptide of LTB in the wide-host range plasmid pMMB68. The CTB gene from pCVD30 (originating from *V. cholerae* 01 strain 0395, classical biotype, Ogawa serotype) has an NdeI site at the position for amino acid (aa) 18 of the leader peptide while the LTB gene has a SaI recognition sequence at the beginning of the mature protein. Fusion of the CTB gene by its 5' NdeI end to the 3' SacI end in the LTB gene, via a synthetic linker as shown in FIG. 1A led to substitution of the CTB leader peptide by that in LTB. In FIG. 1A, the nucleotides underlined with open squares indicate the DNA from the LTB gene, those underlined with filled squares are the synthetic oligodeoxynucleotide part of the linker and those underlined by triangles denote the CTB gene DNA. The numbering over the amino acids refers to their former positions with respect to the first amino acid (+1) in their respective mature proteins. The asterisks indicate amino acids not originally encoded by any of the two fused genes. The synthetic linker restored the SacI site and introduced a SmaI recognition sequence. After the fusion, a plasmid encoding CTB from tacp was obtained (see FIG. 1B below). The sequence shown has been confirmed by dideoxynucleotide sequencing. The resulting plasmid pJS162, which is shown in FIG. 1B, contained the hybrid CTB gene as an EcoRI-HindIII DNA segment downstream the tp promoter. In FIG. 1B the plasmid has an RSF 1010 origin of replication and is approximately 10.2 kb in size. The large arrow denotes the position of the tacP promoter. The starred box represents the gene portion encoding mature CTB. The section encoding the leader peptide (originating from LTB) is symbolized with the filled box. Approximate positions of the ampicillin resistance and the $lacI^q$ genes are indicated.

The following procedures were used to obtain the aforementioned constructions. The pMMB68 plasmid in *E. coli* strain HB101 was kindly provided by M. Sandquist, University of Umeå. Plasmid pCVD30 in *E.coli* HB101 was obtained from Dr J. Kaper, University of Maryland, Baltimore, USA. (For detailed description of these plasmids see M. Sandquist et al, J Bacteriol 169:4570–4576, 1987 and J B Kaper et al, Biotechnology 2:345–349, 1984) . The unphosphorylated oligodeoxynucleotides used to join the SacI 3' end of the LTB leader to the 5' NdeI sequence of CTB were purchased as single strands from the Department of Immunology, Biomedical Centre, University of Uppsala. These strands were paired by mixing equimolar amounts of each strand and incubating the mixture overnight at room temperature. The resulting double-stranded oligonucleotide had SacI and NdeI compatible single stranded extensions and could therefore be joined directly to SacI-HindIII restricted pMMB68. Ligation was performed by incubating a 10-fold molar excess of oligonucleotide to plasmid DNA overnight at 4° C. with T4 ligase. To the ligation mixture was then added in equimolar amounts with respect to vector plasmid DNA a purified NdeI-HindIII fragment from plasmid pCVD30 containing the CTB gene, and the ligase reaction was then continued at 4° C. for another 18 hours. The ligated DNA was subsequently transformed into competent *E. coli* HB101 cells with selection for ampicillin resistance (100 μg/ml). All enzymes used in these procedures were purchased from Boehringer Mannheim, GmBH, FRG and were used as recommended by the supplier. Purification of plasmid DNA was done with the alkali-lysis method, and transformation into *E.coli* with the calcium-rubidium chloride method according to the detailed descriptions of T Manniatis et al, Molecular Cloning. A Laboratory Manual, Cold Spring Harbor Laboratory, 1982.

To verify that the predicted sequences had been generated after cloning the hybrid gene was subcloned into M13 and sequenced by the dideoxynucleotide method of F Sanger et al, Proc Natl Acad Sci, USA 74:5463–5467, 1977. The sequence determined confirmed the sequence reported for the LTB leader portion (J Leong et al, Infect Immun 48:73–77, 1985) and showed a high degree of overall homology with previously reported El Tor and classical CTB mature sequences (M L Gennaro & P Greenaway, Nucleic Acids Res 11:3855–3861, 1983; H Lockman & J B Kaper, J Biol Chem 258:13722–13726, 1983; J J Mekalanos et al, Nataure 306:551–557, 1983; A Kurosky et al, J Biol Chem 252:7257–7264, 1977; C Y Lai, J Biol Chem 252:7249–7256, 1977). A comparison between our recombinant CTB (from a *V. cholerae* 0395 classical strain) and those other sequences is presented in FIG. 2. In FIGS. 2A and 2B, only the anti-sense strand is shown and the amino acids encoded are presented above their respective codons. The Thr residue numbered +1 is the first as normally found in mature CTB while the Ala residue at position −7 (or +1 in brackets) is the first amino acid in mature LTB. Amino acids not initially present in any of the two proteins are indicated by asterisks. A potential ribosome binding site (Shine Dalgarno sequence) is underlined (SD). The vertical arrows indicate the peptide bonds cleaved to release the mature recombinant CTB. Amino acids in the 569B CTB protein sequence which disagree with those predicted by the CTB DNA sequence are in brackets, residues in the CTB from El Tor strains which differ from ours and those in classical 569B CTB are in brackets and in bold type.

1.2. Expression of the tacP controlled CTB gene in *V.cholerae*

Plasmid pJS162 containing the CTB gene under the control of tacP (FIG. 1) was transferred by conjugation from a helper *E. coli* strain, S17-1 (R Simon et al, Biotechnology 2:784–791, 1983) to either the *V. cholerae O*1 strain JBK70 (El Tor biotype) (J B Kaper et al, Nature 308:655–658, 1983) or other El Tor or classical *V. cholerae* strains. To achieve this transfer pJS162 plasmid DNA was first reisolated from *E.coli* HB101 and introduced into *E. coli* S17-1 by transformation using the same procedures from Manniatis et al (1982) as referred to in section 1.1. above. The transformed S17-1 cells were then used as donor organisms in conjugation experiments with the various *V. cholerae* recipient strains. Conjugations were performed as follows. The transformal S17-1 donor organisms and the recipient *V. cholerae* cells were grown in 10 ml LB medium supplemented with the appropriate antibiotics at 37° C. overnight without shaking. From each culture 3 ml of bacterial suspension were then pushed through a Millipore® filter type GS 0.22 m with the aid of a syringe, first the donor and then the recipient cell culture, thus bringing these cells in close contact with each other on the filter surface. The filter was then gently placed on an LB agar plate without antibiotics and incubated at 37° C. for ca 3 hours. Thereafter the filter was transferred into a test tube containing 5 ml LB broth, bacteria were suspended by shaking the tube, and ca 0.1 ml of the mixed bacterial suspension was then incubated in LB broth with appropriate antibiotic counterselection of the donor cells. The bacterial mixture was grown in LB broth containing 50 U/ml polymyxin B and 100 μg/ml ampicillin for counter-selection of the donor when *V. cholerae* strains of the El Tor biotype were the recipients of pJS162. When the plasmid was transferred to *V. cholerae* strains of the classical biotype rifampycin-resistant derivatives of these strains were first isolated, and selection for the recipient rifampycin-resistant vibrio strains in these instances was then done using LB broth containing 50μg/ml of rifampycin and 100 μg/ml of ampicillin.

The production of CTB from *V.cholerae* strains harbouring the pJS162 plasmid was determined as follows. For induction with isopropyl-β-D-thio-galactopyranoside (IPTG) cultures were grown at 37° C. to the desired optical density ($A_{600}$) in LB broth supplemented with antibiotics and then IPTG was added to the desired concentration. Growth was continued for four hours and the cells and culture supernatants separated by centrifugation. Cell pellets were gently washed and resuspended in one original volume of cold phosphate buffered saline pH 7.2 and then broken by two 30 seconds sonic bursts using a miniprobe (Branson sonifier). The levels of CTB in culture supernatants and broken cells were afterwards determined by the GM1-ELISA method with use of the monoclonal antibody LT39 (A-M Svennerholm & J Holmgren, Curr Microbiol 1:19–23, 1978). Conjugal transfer of pJS162 to the toxin-deleted JBK70 *V. cholerae* strain led to production of 40–50 μg/ml of CTB from this strain after growth in LB medium and induction with IPTG; more than 95% of this CTB was secreted into the culture medium (FIG. 3). FIG. 3 shows the induction of CTB expression by IPTG in *V. cholerae* JBK70 (pJS162). Levels of CTB (ordinate), expressed as equivalents of the purified 569B CTB protein, were determined by GM1-ELISA using a specific monoclonal antibody. The actual concentrations in the cell pellets were tenfold lower than shown in the graph (cells×10). Expression of CTB to levels up to 50–100 μg/ml was also achieved in other toxin- or CTA-deleted classical and El Tor strains to which the pJS162 plasmid had ben transferred when these strains were grown in the presence of IPTG (Table 1). This represented a marked overexpression of CTB in comparison with the levels produced by many wild-type or recombinant *V. cholerae* strains examined including the hypertoxigenic 569B strain that is currently used for the preparation of CTB for vaccine production. Since the recombinant CTB encoded by pJS162 was secreted extra-cellularly when produced by *V. cholerae*, it could then readily be purified in high yield from the culture supernatants of either of these strains using e.g. receptor-specific affinity chromatography on lyso-GM1 ganglioside (17), see Example 4 below.

Example 2

OVEREXPRESSION OF CTB BY USE OF A CONSTITUTIVE TACP PROMOTER

In this construction the CTB gene in plasmid pJS162 described in example 1 above, was excised and then inserted into a plasmid vector pKK223-1, which contains the tacP promoter but not the $lacI^q$ gene present in pJS162 that is responsible for IPTG dependence.

The same standard procedures for isolation of plasmid DNA and for DNA excision, ligation, transformation into *E. coli* and conjugation into *V. cholerae* as described in example 1 were used. The CTB gene in plasmid pJS162 was excised as an EcoRI-HindIII fragment and then ligated to EcoRI-HindIII restricted plasmid pKK223-1 (Pharmacia, Uppsala, Sweden), which contains the tacP promoter upstream the EcoRI site. This generated plasmid pJS7523-1 which was brought into *E. coli* HB101 by transformation, and also transferred into *V. cholerae* strains JBK70 and JS1395 by conjugation with the aid of the *E. coli* helper strain S17-1. The $lacI^q$ gene in pJS162 encodes for large amounts of the lacI repressor and the absence of this gene in plasmid pJS7523-1 results in nearly IPTG independent expression of CTB under the control of tacP by bacterial strains harbouring the pJS7523-1 plasmid. This was tested by growing *E. coli* 101 cells harboring pJS7523-1 in LB broth supplemented with 100 μg/ml ampicillin at 37° C. to an optical density of $A_{600}$ 1.0 in duplicate sets of test tubes, and then adding IPTG at 100 μg/ml to one set but not to the other continuing incubation of the bacterial cultures for another 4 h at 37° C. Culture samples were then exposed to ultrasonication by two 30 sec sonic bursts using a miniprobe (Branson sonifier) in order to disrupt the cells, and after centrifugation the ultrasonicated cultures were analysed for their contents of CTB using the GM1-ELISA method also described in example 1). The results obtained showed that relatively high levels, 2–7 μg/ml, of CTB were produced in the absence of any IPTG, and these levels were only 2–3 times lower than those attained in the presence of IPTG. This contrasts dramatically with the effect of IPTG on expression of CTB under control of tacP in pJS162 where in the absence of IPTG the levels of CTB are undetectable (see Example 1, FIG. 2). Thus, although CTB expression in pJS7523-1 is still regulated by the lacI lactose operon repressor these results show that the expression is practically constitutive. This is probably due to the fact that the chromosomally encoded lacI repressor is not produced in sufficient amounts to bind efficiently to both the lac operator in the chromosome and tacP in the high copy number plasmid pJS7523-1.

Example 3

EXPRESSION OF CTB FROM THE T7 RNA POLYMERASE-DEPENDENT PROMOTER

In this example we document that it is also feasible to achieve overexpression of CTB by bringing the CTB gene under expression control of another strong foreign (non-cholera toxin) promoter, the T7 RNA polymerase-dependent promoter.

The structural gene for CTB (including the LTB leader peptide encoding sequence) contained in plasmid pJSl62 was reexcised and inserted into the T7-5 plasmid vector that contains the highly specific and strong T7-RNA polymerase-dependent promoter (S Tabor and C C Richardson, Proc Natl Acad Sci USA 82:1074–1078, 1985). Expression from this promoter requires the presence of the T7 RNA polymerase which is supplied with the help of a complementing plasmid (pGP1-2); the RNA polymerase encoded by this plasmid is itself expressed under control of a promoter which can be induced by a shift in growth temperature (usually from 30° C. to 42° C.)

The methods used for isolation of plasmid DNA and for DNA excision, ligation, transformation into *E. coli* and conjugal transfer into *V. cholerae* were essentially the same as those described in example 1. The CTB in pJS162 was excised as an EcoRI-HindIII fragment which was then inserted into EcoRI-HindIII digested plasmid vector pT7-5 (obtained from Dr S Tabor, Harvard University, Mass., USA). The resulting new plasmid was then transformed into *E. coli* 101 containing plasmid pGP1-2 (also obtained from Dr Tabor). When these transformed *E. coli* organisms were grown in LB broth supplemented with appropriate antibiotics in relation to the two types of plasmids contained in the cells (kanamycin 50 μg/ml; ampicillin 100 μg/ml) the cells did not produce detectable levels of CTB at 30° C., while a subsequent shift in growth temperature from 30° C. to 42° C. led to expression of 2–3 μg/ml of CTB in *E. coli* as assayed with GM1-ELISA. The CTB gene together with the T7 RNA polymerase-dependent promoter was then also subcloned as a PvuII-HindIII insert into EcoRV-HindIII digested plasmid pBR325. The new plasmid (pJS7525) was then mobilized from an *E. coli* strain containing plasmid pRK2013 into *V. cholerae* JBK70 to which the plasmid pGP1-2 had been previously transferred by conjugation from the same *E. coli* donor. The presence of the two plasmids was possible because they have compatible origins of replication and because pJS7525 encodes resistance to chloramphenicol (and ampicillin) while pGP1-2 has the gene for kanamycin resistance. When *V. cholerae* JBK70 containing plasmids pJS725 and pGP1-2 were grown in LB broth supplemented with 25μg/ml of chloramphenicol and 50 μg/ml of kanamycin to a high optical density at 30° C. the organisms produced undetectable levels of CTB, while a shift in growth temperature to 42° C. resulted in the predicted T7 RNA polymerase-dependent increase in CTB expression to levels of 75–100 μg/ml of CTB in the *V. cholerae* culture supernatants. The results described in this example definitely proved both that overexpression of CTB by various foreign (non-cholera toxin) promoters is indeed possible and that overexpression is independent of the toxR regulatory system since one of the factors that leads to high expression of CTB, as affected by toxR, is a growth temperature of around 30° C. (M J Betley et al, Ann Rev Microbiol 40:577–605, 1986). The inducible system here described was minimal at the optimal temperature for toxR and maximal at a toxR-nonoptimal temperature.

Example 4

CHARACTERIZATION OF RECOMBINANT CTB ENCODED BY PLASMID PJS162 IN *V.CHOLERAE*

We have characterized some of the properties of recombinant CTB prepared with the aid of the constructions described in the previous examples. Our results, as exemplified here with purified CTB encoded from plasmid pJS162 expressed in *V. cholerae* JBK70, demonstrate that the recombinant CTB, despite a few amino acid differences, is not appreciably different from CTB purified from wild-type *V. cholerae* 569B cholera toxin in any of the structure-functional and immunological properties tested.

4.1. Purification of CTB and amino-end determination

*V. cholerae* El Tor JBK70 organisms harbouring plasmid pJS162 were grown at 30° C. with continous shaking in 2 l LB medium containing 100 $\mu$g/ml ampicillin and 100 $\mu$g/ml IPTG. After culture, the bacteria and bacterial debris were removed by centrifugation and the recombinant CTB purified by affinity chromatography on a lyso-GM1 ganglioside-Spherosil® column using the procedure described by J L Tayot et al, Eur J Biochem 113:249–258, 1981. Purified CTB was subjected to determination of the amino-end residues as described by H von Bahr-Lindstrom et al, J Prot Chem 1:257–262, 1982.

Cleavage of the precursor peptide of the recombinant CTB would have been naturally predicted to take place at either one or both of the original leader peptidase recognition sites in LTB or CTB. Identification of the first aa in the purified protein gave both Tyr and Ala residues. This and the fact that the recombinant CTB was slightly larger than native CTB as determined by sodium dodecyl sulphate polyacrylamide gel electrophoresis ($NaDodSO_4$/PAGE), see FIG. 4, suggested that proteolytic processing of the leader peptide had taken place between the Gly encoded by the linker (position −5) and Tyr −4 as well as between this latter aa and Ala −3 see FIG. 4. FIG. 4 shows a PAGE of boiled and unboiled samples of CTB. Equal amounts of recombinant CTB protein (lanes 1 and 2) or reference 569B CTB (lanes 3 and 4) were electrophoresed in a 13.5% polyacrylamide $NaDodSO_4$ gel after treatment in sample buffer for 5 minutes at 100° C. (lanes 1 and 3) or at room temperature (lanes 2 and 4). A molecular weight marker (Bio-Rad) with the approximate sizes of protein standards (kDa) is shown (MW). The slower migration of the recombinant CTB as compared to the 569B CTB is only slightly noticeable when examined as the monomers ($B_m$) but is more obvious in the oligomeric (pentameric) forms ($B_p$). When the remainder of the treated CTB was again subjected to amino-end determination Ala and His residues were now identified confirming the postulated cleavage positions and providing evidence that the recombinant CTB carried short peptide extensions at its amino-end consisting of either 3 or 4 aa.

4.2. Receptor recognition and receptor blocking properties

The presence of the few extra aa in the CTB did not affect its recognition of the GM1 receptor. The binding affinity for plastic-coated GM1 ganglioside was compared for the recombinant CTB and purified reference CTB from strain 569B (gift from Dr J Armand, Institut Mérieux, France) by testing different concentrations using the GM1-ELISA method and no difference was revealed. Retention of high binding affinity for GM1 ganglioside was in fact also taken advantage of in the purification of CTB on lyso-GM1-Spherosil® as described above.

Experiments were also performed to determine the ability of the recombinant CTB as compared to 569B CTB to block cholera toxin receptors in the intestine of rabbits. These experiments were done in such a way that either of the CTB preparations were injected into ligated intestinal loops in the animal ca 10 minutes before the injection of a dose (0.2 $\mu$g) of purified cholera toxin known to induce massive intestinal fluid secretion (experimental cholera) in the absence of specific receptor blocking (the detailed procedures have been described by J Holmgren et al, Infect Immun 38:424–433, 1982). The results obtained showed that the recombinant and 569B CTB preparations had similar receptor-blocking activity. Both preparations were able to completely prevent cholera secretion when added to ca 5-cm long ligated intestinal loops in an amount of 50 $\mu$g in 1 ml volume just prior to the injection of cholera toxin (from 569B *V. cholerae*) into the loops. In control loops is pretreated with buffer alone instead of CTB and then injected with the same dose of cholera toxin there was a marked fluid accumulation, 1.7±0.2 ml/cm, and in loops pretreated with 10 $\mu$g or lower amounts of CTB before the toxin challenge there was partial or no reduction of fluid accumulation compared with the buffer-pretreated controls.

4.3. Oligomerization and ability to associate with A subunit

In other experiments it was shown that the recombinant CTB was also unaffected in its ability to both oligomerize and associate with A subunit of cholera toxin (CTA). For these studies purified CTA (prepared from 569B CT; List Biological Laboratories) was mixed with purified recombinant or 569B CTB in the molar CTB to CTA ratio normally found in intact CT to give a total protein concentration of 200 $\mu$g/ml. After mixing, samples were acidified with 0.2 M glycine buffer pH 2.7 and then neutralized by dialysis overnight against several changes of 0.05 M Tris buffer pH 8.0. The neutralized samples were then tested by GM1-ELISA with subunit-specific monoclonal antibodies as described by S J S Hardy et al, Proc Natl Acad Sci USA, in press 1988. The amounts of 569B CTA that associated with recombinant or 569B CTB to give holotoxin were calculated using untreated homologous cholera toxin as reference. The results are shown in table 2. They demonstrate a high recovery of immunoreactive CTB, which is a direct measure of pentameric rather than monomeric CTB since the detecting CTB-specific monoclonal antibody is known to only react with the B pentamer form. They also demonstrate a high recovery of immunoreactive CTA, which is a direct measure of the amount of CTA associated with CTB since unassociated CTA would not bind to the GM1-coated plastic wells and thus be undetected. The recombinant CTB and the purified reference 569B CTB behave very similarly in these experiments (Table 2).

4.4. Immunological properties of recombinant CTB

Adult rabbits were given three subcutaneous immunizations with 30 $\mu$g of the recombinant CTB or 569B CTB with intervals of 2 weeks between injections. The proteins were given with complete Freund's adjuvant in the first inoculation and then with incomplete adjuvant. Two weeks after the third immunization the animals were bled and serum was collected for analysis.

Double diffusion-in-gel immunoprecipitation analyses ad modum Ouchterlony were performed using the microchamber system described by C. Wadsworth, Int Arch Allergy 17:165–177, 1957. The studies were performed with the purified recombinant CTB and 569B CTB and their coresponding rabbit immune sera as reactants. The results showed immunoprecipitation bands of coalescence without any "spurs" between the recombinant and native CTB indicating immunological identity (FIG. 5). FIG. 5 shows an Ouchterlong double-diffusion-in-gel analysis of 569B CTB (wells B and F) and recombinant CTB (wells G and D) reacted with rabbit antisera (wells A and E are antirecombinant CTB and well C is anti-569B CTB).

Titration of antitoxin antibodies in the rabbit immune sera against recombinant and 569B CTB, respectively, was performed by GM1-ELISA using purified recombinant and 569B CTB as antigens attached to GM1 coated plates (A-M Svennerholm et al, J Infect Dis 147:514–521, 1983). The anti-CTB titers in GM1-ELISA were similar, ranging between $4\times10^5$–$1\times10^6$, for anti-recombinant and anti-569B CTB as tested with either of the two CTB preparations as solid phase antigen.

Neutralizing antibodies were assayed by the skin test method of J P Craig (Nature 207:614–616, 19651) using purified 569B CT as test toxin. Heat-inactivated serum was mixed in serial dilutions with equal volumes of purified 569B, CT, 40 ng/ml in physiological phosphate buffered saline supplemented with 10 mg/ml of bovine serum albumin, and 0.1 ml of the mixture was then tested for residual toxicity by intradermal injection. The neutralizing antitoxin titers also did not differ between the sera against either recombinant CTB or 569B CTB. Both types of antisera were able to completely neutralize 2 ng of CT at concentra-tions down to $1\times10^{-4}$.

Example 5

TACP-DIRECTED OVEREXPRESSION OF A HYBRID CTB GENE FUSION PROTEIN

The manipulations described described in example 1 to place the CTB gene under tacP control included, by design, the introduction of single enzyme restriction sites for gene fusions to the CTB amino-end. Cloning into these sites allows construction of CTB-derived hybrid proteins carrying e.g. various putative vaccine peptide antigens that are also under the same expression control of foreign promoters, e.g. tacP, as described for CTB itself in the previous examples. The feasibility of this approach is exemplified here by the fusion of a heat-stable *E.coli* enterotoxin (STa)-related peptide encoded by synthetic oligodeoxynucleotides to the amino-end of CTB in a tacp-directed overexpression system.

5.1. Description of construction

Plasmid pJS162 which contains single SacI and XmaI (SmaI) restriction sites at the junction between the leader peptide and mature CTB (see FIG. 1B) was digested with the corresponding two enzymes and ligated to a synthetic oligodeoxynucleotide encoding the STa-related decapeptide Cys-Ala-Glu-Leu-Cys-Cys-Asn-Pro-Ala-Cys via the SacI and XmaI compatible ends (see FIG. 6). The resulting pJS8 plasmid thereby was provided, under the control of the tacP promoter, with a hybrid gene encoding a fusion protein where the STa-related decapeptide, flanked by a few extra amino acids, was covalently linked to the amino-end of mature CTB as indicated in FIG. 6. In FIG. 6, the synthetic oligodeoxynucleotide (indicated by with single stranded extensions compatible to SacI XmaI restriction ends) was inserted at the DNA region encoding the amino end of CTB in plasmid pJS162. Insertion of the synthetic oligonucleotide was performed so as to maintain the original reading frame in the CTB gene and resulted in a hybrid gene encoding a fusion protein containing a peptide extension comprising an STa-related peptide (indicated by asterisks) at the amino-end of CTB (amino acid indicated by the +1 number). The amino acids indicated with (+) are amino acids encoded by the indicated oligonucleotide which are not considered to be part of the STa-related decapeptide. Upstream to the first amino acid (Arg) there is a leader peptide for CTB originating from a gene encoding LTB, a ribosome binding site (S/D) and the tacp promoter for expression of the hybrid gene (see Plasmid pJS162 in FIG. 1B). The sequence of the fused STa-related decapeptide was identical to a region in native STa except for the substitution of a cysteine residue by alanine. The sequence chosen was based on the previous finding of the capacity of a non-toxic synthetic nonadecapeptide which contains this amino acid replacement to specifically bind an anti-STa monoclonal antibody with ability to neutralize *E.coli* STa (A-M Svennerholm et al, FEMS Microbiol Lett, in press 1988). The sequence fused here is, however, shorter and comprises only 10 amino acids including four cysteines.

The experimental procedures and reagents used in this construction were as specified below. The *E. coli* strain HB101 was used as transient host for plasmid isolations. The *V. cholerae* strain JS1569 is a rifampycin-resistant derivative of strain CVD103. The *E. coli* S17-1 was used for conjugal transfer of plasmids to strain JS1569. The source and further properties of these strains were described in example 1. Isolation of plasmid DNA by the alkali-lysis method including centrifugation in CsCl/ethidium bromide gradients, DNA transformations into *E. coli* and conjugations into *V. cholerae* were also performed according to Maniatis et al (1982) and as specified in example 1. Conditions used for restriction and ligation of DNA were as recommended by the suppliers of the different enzymes. Enzymes were purchased from Boehringer-Mannheim and New England Biologics. The synthetic oligodeoxynucleotides encoding the STa-related decapeptide and adjacent amino acids were purchased as complementary individual strands from Department of Immunolgy (Dr Lena Samuelsson), Biomedical Centre, Uppsala, Sweden. After pairing at room temperature under conditions described in example 1, the synthetic double-stranded oligodeoxynucleotide contained single-stranded ends compatible with SacI at the 5' end and with XmaI at the 3' end.

5.2 TacP-directed expression of ST decapeptide-CTB fusion protein

Cultures of *E.coli* 101 or *V.cholerae* JS1569 harbouring the pJS8 plasmid were grown overnight or until they reached the desired Optical Density (600 nm) with continuous shaking at 37° C. (*E. coli*) or at 30° C. (*V. cholerae*) in liquid LB medium containing ampicillin (100 μg/ml) and/or rifampycin (50 μg/ml) as appropriate. Induction of expression from the tacP promoter by isopropyl-β-D-thio-galactopyranoside (IPTG) was achieved either by its addition at the start of the culture (0.4 mM final concentration) or by first growing the strains to $O.D._{600}$ 0.5 in absence of the inducer and then adding IPTG and continuing cultivation for another 4 hours before harvesting. After growth the bacterial cells and culture supernatants were separated by centrifugation for 5 minutes in a microcentrifuge (Eppendorf). Cell pellets were resuspended in cold phosphate-buffered saline (pH 7.2) and disrupted by two 30 seconds sonic bursts (Branson sonifier). Detection of STa and CTB antigens in supernatants and cell sonicates was done by GM1-ELISA as described using monoclonal antibodies directed against native STa and CTB respectively (J Sanchez et al, FEBS Letters 208:194–198, 1986).

The STa-related decapeptide-CTB hybrid encoded by pJS8 were initially identified in transformed *E.coli* 101 grown in the presence of IPTG as described above. Plasmid pJS8 was subsequently transferred by conjugation from a helper *E. coli* strain (S17-1) to *V. cholerae* JS1569 (using the same procedures as described in example 1). The expression of the hybrid gene in this organism was then studied after culture with addition of different concentrations of IPTG during the logarithmic phase of growth and the cellular localization of the decapeptide-CTB protein was determined as well in a similar manner as described for CTB alone in example 1. The results are shown in FIG. 7. Cells were grown in liquid medium to $OD_{600}$ 0.5 in the absence of inducer and then IPTG was added at the indicated concentrations and cultivation of bacteria continued for another 4 hours before bacterial cells and culture supernatants were harvested. Levels of hybrid protein (ordinate) were determined by GM1-ELISA using a specific monoclonal anti-STa antibody (ST 1:3 kindly provided by a Dr. A-M Svennerbholm, Goteborg, Sweden). A purified STa-related decapeptide-CTB hybrid protein preparation was used as a reference. Stars denote concentrations of hybrid protein in supernatants and open squares denote cell-associated concentrations determined after disruption of the cells by ultrasonication. The results in FIG. 7 show that the hybrid protein was produced in a clearly IPTG-dependent manner and was fully secreted to the extracellular milieu. This location of the decapeptide-CTB allowed for its purification by lyso-GM1 affinity chromatography in the same manner as described for recombinant CTB alone in example 4.

5.3. Properties of gene fusion decapeptide-CTB hybrid protein

To study the properties of the decapeptide-CTB the hybrid protein was purified from culture supernatants of *Vibrio cholerae* strain JS1569 harbouring plasmid pJS8 by single-step affinity chromatography essentially according to J L Tayot et al, Eur J Biochem, 113:249–258, 1981.

Five μg of the purified protein or reference CTB were then subjected to electrophoresis on 13.5% SDS-polyacrylamide gels in the absence of β-mercaptoethanol. Protein samples were either boiled or left at room temperature in sample buffer before electrophoresis so as to analyse the proteins in their pentameric and monomeric forms (see T R Hirst & J Holmgren, Proc Natl Acad Sci USA, 84:7418–7422, 1987). The separated proteins were then electrotransferred to nitrocellulose for reaction with anti-STa or anti-CTB monoclonal antibodies followed by incubation with anti-mouse IgG coupled to peroxidase (Jackson Biologicals). Immunoreactive protein bands were finally developed using α-chloronaphtol substrate.The results are shown in FIG. 8. In FIG. 8, lanes A–D show reaction patterns of unboiled purified 569B CTB (lane A), boiled CTB (lane B), unboiled STa-related decapeptide-CTB (lane C) and boiled STa-related decapeptide-CTB (lane D) after development with anti-cholera toxin monoclonal antibody Wi7:5. Lanes E–H show the reaction patterns obtained for the same proteins after development with anti-STa monoclonal antibody 1:3. Arrows refer to the migration positions of reference proteins with known molecular weights (indicated as Kilodaltons) run on the same gel. Reaction with anti-CTB revealed bands at the positions expected for the pentameric forms of the control CTB or STa-related decapeptide-CTB hybrid protein. Incubation of the respective boiled and unboiled samples with anti-STa monoclonal antibody developed bands corresponding to the pentameric and monomeric forms of the decapeptide-CTB protein but gave a negative reaction with either the pentameric or monomeric forms of the control CTB. The monomeric form of CTB did not react with anti-CTB whereas a minor reaction of the monomeric form of the decapeptide-CTB with this antibody was observed.

The decapeptide-CTB protein exhibited no toxicity as tested in amounts up to 10 μg in the infant mouse intragastric injection assay performed as described by A-M Svennerholm et al, FEMS Microbiol Letters, in press, 1988. Concurrently tested purified native STa (obtained is from Dr A-M Svennerholm) gave positive infant mouse tests in amounts down to 1 ng, i.e. a 10,000-fold lower dose. The STa-related decapeptide-CTB hybrid protein was able to efficiently bind anti-STa monoclonal antibodies both in GM1-ELISA and in immunoblot analyses; see FIGS. 7 and 8. The hybrid protein exhibited, in addition, a number of attributes characteristic of the CTB moiety such as the ability to pentamerize, to bind to the GM1 receptor and to be secreted by *V. cholerae*; these properties were assayed using methods described in example 4 for recombinant CTB alone.

When the purified protein was used to immunize rabbits it gave rise to antibodies which cross-reacted with native STa. The anti-STa titer determined by ELISA using synthetic, plastic-coated STa as solid-phase antigen rose from an undetectable level in preimmunization serum to a titer of 1:2000 after three subcutaneous immunizations, which compared favourably with the titers attained in rabbits by immunization with a chemically derived hybrid protein carrying native STa. The immunogenicity together with the lack of toxicity of the STa-related decapeptide-CTB protein and its ability to recognize the GM1 intestinal receptor make the hybrid protein a candidate toxoid for oral immunization against STa-associated *E. coli* diarrhoea in animals and humans.

We claim:

1. A method of producing a fusion protein, said fusion protein comprising a cholera toxin B subunit and a peptide having a smaller molecular weight than said cholera toxin B subunit, said method com ing the steps of:

introducing into a host cell a nucleic acid expression vector, said expression vector comprising a promoter and a ribosomal binding site in operative association with a nucleotide sequence encoding a polypeptide comprising a leader peptide and said fusion protein, wherein said promoter is not of *Vibrio cholera* origin and wherein there is no nucleotide sequence of *V. Cholera* origin between said promoter and said ribosomal binding site; and culturing said host cell under conditions which permit the expression of said fusion protein.

2. The method of claim 1, wherein said promoter is inducible.

3. The method of claim 1, wherein said promoter is tacP.

4. The method of claim 1, wherein said leader peptide is from an enterotoxin.

5. The method of claim 4, wherein said leader peptide is from the *E. Coli* enterotoxin LTB.

6. The method of claim 1, wherein said peptide sequence comprises the amino acid sequence Cys-Ala-Glu-Leu-Cys-Cys-Asn-Pro-Ala-Cys.

7. The method of claim 1, wherein said host cell is from the genus Vibrio.

8. The method of claim 7, wherein said host cell is *Vibrio Cholerae.*

9. A composition comprising a fusion protein produced by the method of claim 1, in combination with a pharmaceutically acceptable carrier.

10. A host cell transformed with a nucleic acid vector comprising a promoter, a ribosome binding site, a leader peptide coding sequence, a cholera toxin B subunit coding sequence and a peptide coding sequence, wherein said promoter is of non-*V. cholera* origin and said leader sequence, ribosome binding site, cholera toxin B subunit and peptide coding sequences are operably linked in the proper reading frame, and wherein the linking between said ribosome binding site and said promoter is such that no DNA of *V. cholera* origin is between said promoter and said ribosome binding site, and wherein the peptide produced by said peptide coding sequence has a smaller moleclar weight than said cholera toxin B subunit.

11. A method of producing a fusion protein, said fusion protein comprising a cholera toxin B subunit and a peptide having a smaller molecular weight than said cholera toxin B subunit, said method comprising:

obtaining a nucleic acid vector comprising a promoter, a ribosome binding site, a leader peptide coding sequence, a cholera toxin B subunit coding sequence and a peptide coding sequence, wherein said promoter is of non-*V. cholera* origin and said leader sequence, ribosome binding site, cholera toxin B subunit and peptide coding sequences are operably linked in the same reading frame, and wherein the linking between said ribosome binding site and said promoter is such that no DNA of *V. cholera* origin is between said promoter and said ribosome binding site;

introducing said nucleic acid vector into a host cell; and producing said fusion protein.

12. The method of claim 11, wherein said peptide coding sequence is derived from a sequence encoding heat stable *E. coli* enterotoxin.

13. The method of claim 11, wherein said promoter is tacP.

14. A method for inducing production of antibodies against a peptide in a mammal, comprising:

administering to said mammal the fusion protein produced by the method of claim 11, in an amount sufficient to elicit production of antibodies against the peptide translated from said peptide coding sequence in said mammal.

15. The method of claim 14, wherein said peptide is derived from heat stable *E. coli* enterotoxin.

16. The method of claim 15, wherein said peptide comprises the amino acid sequence Cys-Ala-Glu-Leu-Cys-Cys-Asn-Pro-Ala-Cys.

17. The method of claim 14, wherein said administration is oral.

18. A composition comprising a fusion protein produced by the method of claim 11, in combination with a pharmaceutically acceptable carrier.

19. The composition of claim 18, wherein said peptide is derived from heat stable *E. coli* enterotoxin.

20. The composition of claim 19, where said peptide comprises the amino acid sequence Cys-Ala-Glu-Leu-Cys-Cys-Asn-Pro-Ala-Cys.

21. A method of producing a fusion protein, said fusion protein comprising a cholera toxin B subunit and a peptide having a smaller molecular weight than said cholera toxin B subunit, comprising:

obtaining a nucleic acid vector comprising a promoter, a ribosome binding site, a leader peptide coding sequence and a cholera toxin B subunit coding sequence, wherein said promoter is of non-*V. cholera* origin;

inserting a peptide coding sequence between said leader peptide coding sequence and said cholera toxin B subunit coding sequence, wherein said leader sequence, ribosome binding site, cholera toxin B subunit coding sequence and peptide coding sequence are operably linked in the same reading frame, and wherein the linking between said ribosome binding site and said promoter is such that no DNA of *V. cholera* origin is between said promoter and said ribosome binding site;

introducing said nucleic acid vector into a host cell; and producing a fusion protein comprising said cholera toxin B subunit and said peptide.

22. The method of claim 21, wherein said peptide coding sequence is derived from a sequence encoding heat stable *E. coli* enterotoxin.

23. The method of claim 21, wherein said promoter is inducible.

24. The method of claim 23, wherein said promoter is tacP.

25. The method of claim 21, wherein said leader peptide is from an enterotoxin.

26. The method of claim 25, wherein said leader peptide is from the *E. Coli* enterotoxin LTB.

27. The method of claim 21, wherein said peptide comprises the amino acid sequence Cys-Ala-Glu-Leu-Cys-Cys-Asn-Pro-Ala-Cys.

28. The method of claim 21, wherein said host cell is from the genus Vibrio.

29. The method of claim 28, wherein said host cell is *Vibrio Cholerae*.

* * * * *

UNITED STATES PATENT AND TRADEMARK OFFICE

CERTIFICATE OF CORRECTION

PATENT NO. : 6,043,057
DATED : March 28, 2002
INVENTOR(S) : Holmgren et al.

It is certified that error appears in the above-identified patent and that said Letters Patent is hereby corrected as shown below:

<u>Column 14,</u>
Line 16, cancel "com ing" and replace it with -- comprising --.

Signed and Sealed this

Twenty-fifth Day of June, 2002

*Attest:*

JAMES E. ROGAN

*Attesting Officer*

*Director of the United States Patent and Trademark Office*

UNITED STATES PATENT AND TRADEMARK OFFICE

CERTIFICATE OF CORRECTION

PATENT NO. : 6,043,057
DATED : March 28, 2000
INVENTOR(S) : Holmgren et al.

It is certified that error appears in the above-identified patent and that said Letters Patent is hereby corrected as shown below:

Column 14,
Line 16, cancel "com ing" and replace it with -- comprising --.

Signed and Sealed this

Twenty-seventh Day of May, 2003

JAMES E. ROGAN
*Director of the United States Patent and Trademark Office*